US012690764B2

(12) United States Patent
Christofferson et al.

(10) Patent No.: US 12,690,764 B2
(45) Date of Patent: Jul. 28, 2026

(54) RETINAL FOVEATION SYSTEM AND METHOD

(71) Applicant: Quantum Radius Corporation, Arvada, CO (US)

(72) Inventors: Frank Christofferson, Arvada, CO (US); Timothy R Wahlers, Green Bay, WI (US); John Ewalt, Broomfield, CO (US); Jeffrey D George, Kent, WA (US); Kevin Bowman, Longmont, CO (US)

(73) Assignee: Quantum Radius Corporation, Arvada, CO (US)

( * ) Notice: Subject to any disclaimer, the term of this patent is extended or adjusted under 35 U.S.C. 154(b) by 182 days.

(21) Appl. No.: 18/273,981

(22) PCT Filed: Jan. 25, 2022

(86) PCT No.: PCT/US2022/013772
§ 371 (c)(1),
(2) Date: Jul. 25, 2023

(87) PCT Pub. No.: WO2022/159912
PCT Pub. Date: Jul. 28, 2022

(65) Prior Publication Data
US 2024/0423465 A1      Dec. 26, 2024

Related U.S. Application Data

(60) Provisional application No. 63/252,628, filed on Oct. 6, 2021, provisional application No. 63/141,440, filed on Jan. 25, 2021.

(51) Int. Cl.
*A61B 3/00* (2006.01)
*A61B 3/14* (2006.01)

(52) U.S. Cl.
CPC ................ *A61B 3/005* (2013.01); *A61B 3/14* (2013.01)

(58) Field of Classification Search
None
See application file for complete search history.

(56) References Cited

U.S. PATENT DOCUMENTS

| | | | | |
|---|---|---|---|---|
| 11,363,282 B1* | 6/2022 | Christofferson | ....... | H04N 19/13 |
| 2012/0105310 A1* | 5/2012 | Sverdrup | ........... | G02B 27/0172 |
| | | | | 345/8 |
| 2017/0263046 A1* | 9/2017 | Patney | ................... | G06T 15/20 |
| 2017/0285343 A1* | 10/2017 | Belenkii | .............. | H04N 13/344 |
| 2018/0262758 A1* | 9/2018 | El-Ghoroury | ........ | G02B 27/017 |
| 2018/0275410 A1* | 9/2018 | Yeoh | ....................... | G06F 3/011 |
| 2019/0102865 A1* | 4/2019 | Hensley | ................ | G06T 15/005 |
| 2019/0287495 A1* | 9/2019 | Mathur | .................. | G06F 3/011 |
| 2019/0379944 A1* | 12/2019 | Christofferson | ........ | H04L 67/10 |
| 2020/0074716 A1* | 3/2020 | Kaplan | ................ | H04N 13/344 |

* cited by examiner

*Primary Examiner* — Hilina K Demeter
(74) *Attorney, Agent, or Firm* — Clyde R Christofferson, Esq.

(57) ABSTRACT

An improved image foveation method is described employing a more complete digital model of the retina and coordination of one or more nodes for foveated image creation, processing, compression and display.

20 Claims, 6 Drawing Sheets

113

111

112

201 202 203 204 205 206

207

Cone isocontour
example Curcio, Sloan

RETINAL FOVEATION SYSTEM AND METHOD

BACKGROUND

The Human Visual System (HVS) is extremely complex and currently only partially understood. Ultimately the HVS tries to make sense of photons entering the eye. Vision is our most powerful natural sensor interface, evolved to create an almost instantaneous direct conduit from the real world to the brain for interpretation. The HVS varies significantly between individuals.

The lessons of vision can largely be generalized and enhanced outside our species and includes artificial sensor and analysis systems. For example, astronomical infrared sensors capture photons with artificial photoreceptors tuned to different wavelengths, image recognition systems attempt to identify objects within scenes that can't be seen with the naked eye, and synthetic renderers can create a myriad of special effects impossible in the real world.

Not only has vision shaped human survival, but it has shaped our culture and commerce. The formulas for creating pigments to richly reflect light in fabrics and surfaces were some of the most valuable commodities throughout civilization. From early cave-drawings to imagery dominating Internet traffic today, the value of human vision is clear.

Image Technology

As complex as vision is, so too is the modern technology chain driving interpretation and synthesis of artificial imagery. A variety of technologies are used to mimic the natural photonic inputs to natural vision. Yet, technology is "flying blind" in many ways regarding imagery, as science has not yet uncovered a complete understanding of the physics, biology and cognitive complexity of vision, nor has been able to duplicate its functions perfectly.

Instruments such as diagnostic retinal cameras have accelerated study and use of vision, as have refinement of MRI (Magnetic Resonance Imaging) of the brain and breakthroughs in optics, machine learning and biology. Dramatic advances in applied technology such as manufacturing, computer processing, memory, storage and networking have improved the practicality and capability of mass-market products related to vision. Tiny manufactured arrays of sensors such as CCDs (Charge Coupled Devices) capture photons, massive parallel processors such as GPUs (Graphics Processing Units) generate synthetic images, complex algorithms and standards such as H.265 are implemented on custom processors to compress imagery, and images are created and guided to the eye through optical waveguides in advanced display systems.

In parallel, advances in technology supporting digital content authoring play an important role as the scale of "digital twins" or artificial worlds increase in complexity and value. From digital paintbrushes to advanced 3D design and authoring tools to lidar and polarized light-based automated scene reconstruction, rapidly evolving technology blends with human creativity to feed the overall image system pipeline.

Image systems are no longer limited or single-purpose and boxed-in systems, as were early digital cameras and early displays. High bandwidth, low latency networks now connect billions of smartphones and powerful cloud services deliver trillions of image pixels. Nearly ubiquitous wireless access points, global satellite communications, and eventual quantum networks open the door to interactive round-trip image systems that can be shared amongst all humanity in near real-time. For the first time, humankind has crossed the technology threshold where delivery of imagery indistinguishable or even superior to lifelike imagery is possible.

Image technology in total is as rich and varied as human vision. Despite our incomplete knowledge of the vision system, humankind has made intuitive and steady progress in creating artificial image systems. A tremendous number of devices are employed to create, process, store, compress, transmit and display imagery, ranging from cameras to synthetic renderers to image encoders to high-resolution displays. An ecosystem of technologies combine to deliver and display streaming movies, interactive games or even a future "metaverse" of virtual environments used for socializing, recreation and work.

Until the limits of human vision and cognition are matched or exceeded by technology, the quest to improve this "reality bridge" between the natural and synthetic world will spawn many innovations.

The Retina

One of the most complex and important visual organs in the vision chain is the retina.

The human retina is a biologic sensor composed of around 100 million photoreceptors and photosensitive ganglia spread throughout its interior spheroid surface. These sensors send information through a complex network with sometimes combinatorial effects, filtering and distributing electrical and chemical interactions. The primary sensor receptors are tuned to specific wavelengths. They have different attributes for different purposes, such as increased photonic sensitivity at low light, color detection or to trigger pupil dilation. The sensors are densely packed throughout the retina but are not uniform, and can vary in performance and proportional density throughout the retina. Different individuals often have varying sensors in type, characteristic and distribution.

Retinal sensors register the energy from photons after they have been focused by the dynamic optics of the eye. The ultimate goal of the system is to transduce that energy to a compressed signal that is sent through the optic nerve to regions of the brain for interpretation and cognition.

Retinal sensors must continuously process photons, as they do not arrive as single images. Signals must be processed within the constraints of the HVS, which includes limits on electrical and chemical response and transmission. Direct sunlight or lasers can exceed the parameters of the evolved system and cause permanent retinal damage, as an example.

Foveation

The term "fovea" describes the central visual focal area of the retina.

"Foveation" is a popularized term coined initially to describe the relationship between foveal focal point and construction of minimal required detail throughout an image. It is commonly employed as imprecise shorthand acknowledging vision has variable spatial attributes, most often oversimplified into a view of "focused" and "blurry" spatial resolution correlated to distance from the focal point.

Most early foveated systems typically applied radial distance functions, simple gaussian filters, or circular zones to approximate decreasing spatial resolution as image construction moved away from the focal point. Until recently, most applications using foveation have implemented relatively straightforward methods to reduce the amount of data needed to represent, analyze or render a synthetic image.

Foveated systems assume a focal point, such as an attention focus or a gaze direction. Accurate, low-latency gaze tracking is required for effective advanced foveation, needed to quickly correlate an image with the current retinal position of the viewer. One reason foveation innovation is accelerating is the recent wide availability of effective eye tracking from companies such as Tobii. These systems not only track the gaze direction, but perform functions such as smoothing over time discretized tracking information, even anticipating motion parameters due to the mechanics of the eye. They also accommodate complex ocular motions such as saccades, know the diameter of the pupil and discern additional useful information such as the depth focal point of stereo vision.

Retinal bandwidth, compression and computation

Understanding and applying vision more fully allows creation of product and service solutions that minimize resource usage and/or maximize fidelity. Were raw, complete data matching photonic impact on HVS retinal sensors used as a benchmark for fidelity, the capabilities and bandwidth requirements of artificially sensing, creating, storing, transmitting and displaying imagery would be untenable currently.

Using current technology matched to raw requirements including real-time response, the needed bandwidth would be on the order of terabits of data per second. In this scenario, database processing and GPU requirements would be nearly infinite. Corresponding cameras and displays would be at the outer bounds of imagined current technology, requiring on the order of 16K resolution and 240 Hz update rates. Using current semiconductor manufacturing technology, power requirements for such systems would also be untenable.

An important sub-specialty of image technology that in part comes to the rescue is video compression. The compression of images and streams of video images has been a robust area of innovation for over 50 years. It is one of the single most patented and litigious areas of technology, corresponding to the market impact of imagery on billions of devices and the many services that dominated broadcast television earlier and now the current pixels comprising the majority of data on the Internet.

Early compression technology such as MPEG evolved into very complex standards such as H.265 and have emphasized compression of imagery for consumer displays and mass-market applications, including mostly televisions, computer monitors and then smartphones.

Not all past image compression is relevant in a foveated world of retinal imagery. Lacking eye-tracking technology, traditional video compression relies on regular, rectangular images of pixels that are all the same. Without knowledge of the fovea, application in these codecs of methods such as the DCT (Discrete Cosine Transformation) and color space manipulation divided and conquered full images and streams of images by breaking them into similar blocks of pixels suitable for iterative algorithms.

To be clear, many custom and advanced features of video codecs identify areas of interest or advanced image processing and provide value to the foveated view of the world, but without user focal point they simply could not design to nor exploit the full features of the retina. For the vast majority of these compression techniques, it was also true that end-to-end compression/decompression latency was not a priority, nor was data-invariant determinism in encoding time. The products and services demanded no more. Those boundaries also limit the full application of the technologies from that era into the forward market of individualized highly interactive image-based services having more flexible foveated imaging and display systems.

New research in metamers highlights both the capability and the limitations of the HVS bandwidth and associated cognitive inference of image recognition. Metamers are stimuli that differ physically but look the same, such as mixtures of shapes or colors that are perceived the same even though they are different.

Fortunately, an example of reduction of both workload and maximal compression is provided by the HVS. The optic nerve is estimated to carry on the order of 10 Mbits/sec, and our cognitive systems have limits and a corresponding surprising capacity to extrapolate, interpolate and distill to fill in the gaps of compressed photonic data.

Historical Context

Gradual progression of the understanding of the HVS goes back millennia to Aristotle and others, literally focusing on optics and perception. Subsequently, the trichromatic theory of color was proposed in 1801 by Thomas Young, and luminaries such as James Clerk Maxwell refined it. More recently, theories such as the Retinex Theory by Land attempted to understand and apply interactions of color and contrast.

Only recently have the tools and cross-discipline techniques existed to fully investigate and attempt to understand the microscopic structure of the retina and its interaction with cognition. All prior work were admirable "shots in the dark".

In the past few decades, products have proliferated that leverage the HVS, ranging from television to TikTok. Progress came with understanding, deep technological innovation and trial and error.

Some of these products and innovations were derived from teachings from over a century of magicians and film special effects seeking to "fool the eye". Digital implementations from companies like Pixar, Lucasfilm, Robert Abel and Associates and others have applied that teaching to a wide variety of rendering and model technology such as lighting special effects, physics simulation and image antialiasing, starting in the 1970s. Subsequently, companies with products in computer-aided design and then interactive gaming software such as Unity or Epic's Unreal have accelerated this trend, often in lockstep with available general-purpose as well as customized hardware.

Hardware supporting the HVS evolved rapidly, as early displays and image frame buffers from companies like Evans & Sutherland and Pixar progressed to more advanced hardware implementations from researchers and companies like Boeing, Dassault and others primarily in the aerospace industry targeting expensive flight simulators. The market progressed with the later entrance of Silicon Graphics into the larger professional workstation market and accelerated at scale with companies like NVIDIA for the consumer market.

More recently, companies such as HP, Meta, Microsoft, NVIDIA, Pico, Tobii and Varjo among others have pushed eye tracking paired with basic foveation into the verge of mainstream usage. Remote rendering technology from those such as Christofferson in the 1990s coupled with modern cloud technology and foveation now presents the opportunity to reach the mass market with HVS-calibrated image systems.

Benefits and Deficiences of Prior Art

The human visual system may not have changed much in millions of years, but a rudimentary understanding of how the HVS works is relatively recent, as is technology that mimics or assists human vision. The myriad of prior technologies and inventions in this field are foundational, yet still can't approach the overall fidelity of the HVS. The invention seeks to build upon those inventions and help bridge that gap.

Of essential benefit to foveation is eye-tracking technology and improvements in inference and performance of that series of inventions.

Inventions in the area of display technology in general and advancements in retinal displays in particular are important. Furness et al describe one of the first direct retinal displays. The current invention learned from this approach to generalize beyond raster displays and be flexible enough to apply to new irregular or custom displays or even optic nerve implants.

Image compression prior art is significant and referenced above.

However, in the view of the invention all prior art in image compression and foveation is like the parable of blind men each feeling a different part of the same elephant. Without a general approach to the HVS and retinal theory in particular, foveation and the entire technology image chain are incomplete.

SUMMARY

The invention seeks to encode descriptions of all sensors and functions of the retina into portable, computationally useful digital maps which are then applied flexibly to an optimized system of extensible foveated imaging. These maps enable the retention, reinterpretation and reuse of core retinal data across distributed image foveation nodes, allowing customization and optimization in a dynamic system.

Unlike current systems, they would explicitly include all available retinal data needed to create optimal imagery. The invention seeks to cross the chasm between the HVS and systems that mimic it by employing portable virtual buffers we call the Hyperpixel Retinal Map (HRM). These maps coalesce any essential knowledge of the HVS in general and the retina in particular into sharable, retained, dynamically interpreted data structures. The HRM consists of the minimal set of interpreted and augmented HVS data which can optimize fidelity and cost in a foveated visual system. A foveated system employing the invention could optimally sense, process, compress and display imagery using any and all resources, or choose any combinatorial variants of those functions and resources.

Motivation

We imagined the challenge of generating billions of "packets of pixels" which correlate to the continuous, nearly unlimited photons impinging on a user retina or sensor. These virtual photons would be sent around sensor or compute nodes spanning devices, networks and clouds, and would usually be assembled ultimately into single user display in real-time. Current foveation and image compression techniques offered keys to implementing such a solution but are insufficient to coordinate this over a network of disparate devices, and do not consider the problems of scale.

One motivation behind the invention was the quest to deliver a range of intentional visual fidelity at real-time rates. In contrast to best-effort current practice, intentional visual fidelity seeks a flexible goal that can be tuned to provide a full range of fidelity. This would allow on one extreme the creation of imagery indistinguishable from or superior to reality, with no perceptual artifacts. This requires a pragmatic way to scale resources to the visual fidelity goal. Alternately, a use would be to optimize fidelity within the constraints of dynamically limited resources, for example based on latency, cost or energy.

We sought to decouple our invention from limitations of former rectangular pixel-based image and display systems with fixed frame rates, preparing for a wide range of alternate display techniques and their intermediate representations. For example, rather than pixel-based rectangular displays, foveation should support varifocal, variable update, variable resolution, wide field-of-view displays, direct external retinal excitation, ocular implants and eventually optic nerve signal injection systems.

We explicitly sought to remove the limitations of prior art in foveation which applies or retains significantly incomplete retinal science information, or eliminates utility by generalizing attributes such as spatial ratios. Much higher granularity and depth of information is required for full utility and re-use and improvement, particular in systems with many attributes that differ between nodes or are dependent on different inputs at different times.

We were also motivated to remove limits in prior art acting as a barrier to application of foveation within a distributed environment, including harmonizing use of foveation across remote sensor capture, rendering, compression, compositing and interaction components, and explicitly removing limits on configuration of multiple sources for creation and fusion of composited imagery.

We learned from and sought to overcome prior art in image compression, having the insight that prior art in image compression essentially attempted to foveate an entire image using a universal focus, which renders some of that effort inapplicable to foveated compression.

We learned from decades of object recognition prior art, which literally focuses on parts of an image with a deliberate deemphasis of the remainder of the image. Instead, with our foveated approach other non-focused parts of the image are "first class citizens" and treated with equally custom but different parameters. This is because what happens elsewhere in the HVS is still perceived but must be treated differently.

In total, we imagined an invention needed to more accurately foveate both relatively simple devices and applications on one extreme and on the other to simultaneously orchestrate complex real-time foveated services implemented with dynamic, distributed, asynchronous, asymmetrical, parallelized, pipelined architectures that can serve the cost-effective mass market or extreme applications at highest fidelity.

Examples of products and services we considered to guide our invention include self-contained retinal-guided binoculars, advanced 3D immersive lowest-latency remote drone-based systems for uses such as firefighting or rescue, featherweight lowest cost/power virtual reality displays which receive extreme fidelity imagery from a wireless service, and eventually quantum communications-based neural retinal-brain augmented interfaces which instantly send imagery superior to reality to even the vision impaired in a highly distributed real-time metaverse service with billions of simultaneous users sharing an enhanced digital universe.

An advanced foveated system as envisioned for the invention offers a key solution to the challenge to produce the lowest cost, the highest fidelity, and the most scalable products targeting the human visual system all at once.

An aspect of the invention is an image foveation system, comprising a hyperpixel system further including a hyperpixel data repository and a hyperpixel retinal map, the hyperpixel retinal map corresponding to a human visual system and mapping to the hyperpixel data repository: a user display system that tracks a user gaze upon an image source enabling the hyperpixel system to distinguish between image source components impinging upon a fovea of a user retina and image source components impinging upon a periphery of the user retina: wherein the hyperpixel system generates for the user display updates to the image source when needed for changes in the user gaze, the updates being responsive to the human visual system of the user as reflected in the hyperpixel retinal map, including at least updates responsive to user sensitivities at the fovea of the user retina and updates responsive to user sensitivities at the periphery of the user retina.

According to a further aspect of the invention, user sensitivities at the fovea of the user retina are translated by the hyperpixel system into more color and higher resolution and update frequencies as compared to user sensitivities at the periphery of the user retina where a higher density of rods reflects heightened sensitivity to motion. In another aspect different user sensitivities at the fovea of the user retina as compared to the periphery of the user retina are translated by the hyperpixel system into updates which are asynchronous across image source components. In yet another aspect of the invention the hyperpixel retinal map enables definition of image source components using isocontours, with updates more frequently for components nearer the fovea and updates less frequently for components further from the fovea.

In a further aspect of the invention processing of different image source components is distributed to different processors. At least some of the different processors can be located in a network cloud. Yet another aspect of the invention provides that the hyperpixel data repository is distributed among a plurality of storage locations. It is also an aspect of the invention that a different temporal density of updating corresponds to different density of rod sensors in different image components being updated. The invention may also be used in a stereo display wherein foveation parameters for each of the stereo displays are distributed to two or more distinct remote rendering systems for processing. The stereo display may include a nasal view occlusion of the user.

BRIEF DESCRIPTION OF THE FIGURES

The disclosure may best be understood by reference to the following description taken in conjunction with the accompanying drawings in which.

DETAILED DESCRIPTION

Terminology

Figure 1:
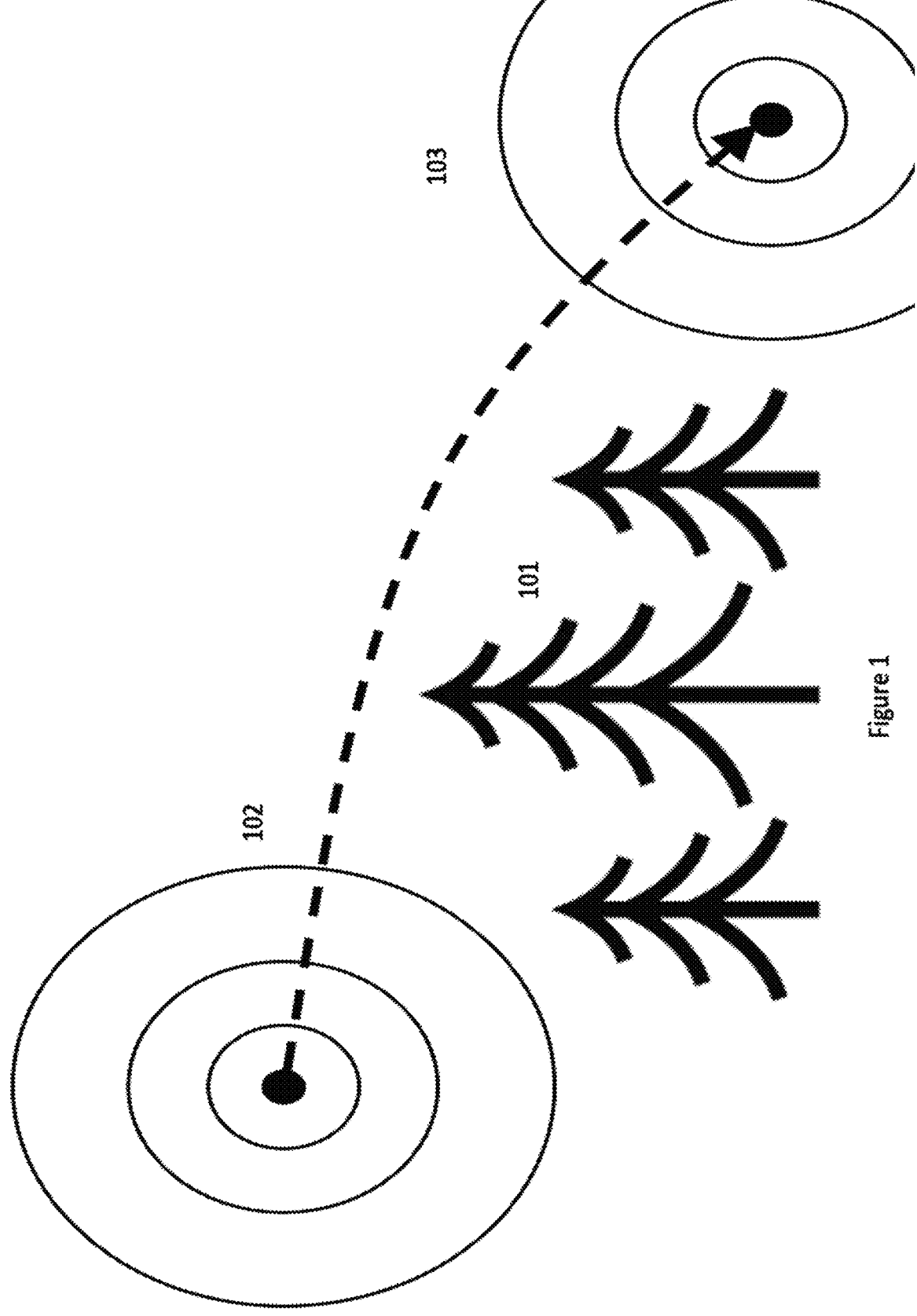
FIG. 1 shows an abstracted view of basic foveation techniques as applied to an image.

Terminology in emerging fields is often fluid and challenging. For the purposes of the present invention certain terms will be used as indicated below:

The components of a rexel described by a one arcsecond squared subtended steradian of the retina might be placed in a hyperpixel data structure and organized into isocontours for parallel processing.

The term "pixel" is commonly understood to refer to individual "picture elements" and is usually associated with rigid rectangular displays composed of illuminated grids of red, green and blue sub-components. It is also used when describing components in buffers ultimately targeting an image, such as used in a pixel shader in a renderer or a CCD sensor element in a camera. This is subtle because it begins to disassociate the display element and the construct used to feed the display. The overloading of the term is also apparent when we consider, "what is a pixel in system which is alpha blended, anti-aliased or scaled?"

The term "steradian" is a 3D angular area projection onto the surface of a sphere, and is analogous to the term radian used in two dimensions. This is a useful as a way to think in terms of angularly defined areas of the spherical-similar retina.

The term "rexel" is a less common and non-standard term that attempts to identify components of retinal vision, which may address an area different from that addressed by a pixel, even if they are later correlated in some way. If the retina is defined mostly by the surface of a hemisphere, a rexel would be a projected area on the interior surface. Perhaps confusingly but also part of the utility of the invention, the same rexel area may include overlapping sensors, ganglia and other features.

The term "hyperpixel" is non-standard, and we apply it liberally here as an abstracted combination of pixel and rexel, enabling a way to talk about various individual components within a system that spans image sensing, processing and display. Pixels are too narrow, as they quickly ascribe spatial and display attributes. Rexels are specific to spatial retinal data, and do not allow for enough embellishment of that data.

The term "isocontour" is a standard term which organizes data into similar values based on some arbitrary threshold or value. Topographic maps use elevation iscontours, and image or retinal maps can distill isocontours based on regional groups of similar color or contrast value, as examples. In the case of the invention, we wish to clearly illuminate that isocontours need not be contiguous, but only similar. Thus, in this use an image of a screen door might define two groups of data that are never contiguous but evenly distributed when organized by isocontour.

DESCRIPTION

A preferred embodiment of the invention employs a master Hyperpixel Retinal Map (HRM) to organize data needed by a distributed foveated system. An HRM can include general data as well as customized data for individual, use case and system. Each node or device is given a copy of the master HRM needed for a service and can update other nodes with its own characteristics to inform them of global optimizations. Any modified or learned data can be incorporated into the improved master HRM.

FIG. 1 shows a typical interpretation of foveation in prior art, where two time-based versions of an image are shown in an abstracted composited fashion. Typically (but not necessarily), an image is produced as a perspective projected view of a scene 101, with the first representation 102 being the initial user view based on an eye tracking foveal position with application of regional spatial foveation and 102 showing the progression of the viewpoint over time to a second view. The intention of common prior art is the central focal circular region of each foveated region is calculated or displayed at higher resolution than subsequent outer regions.

Figure 1A:
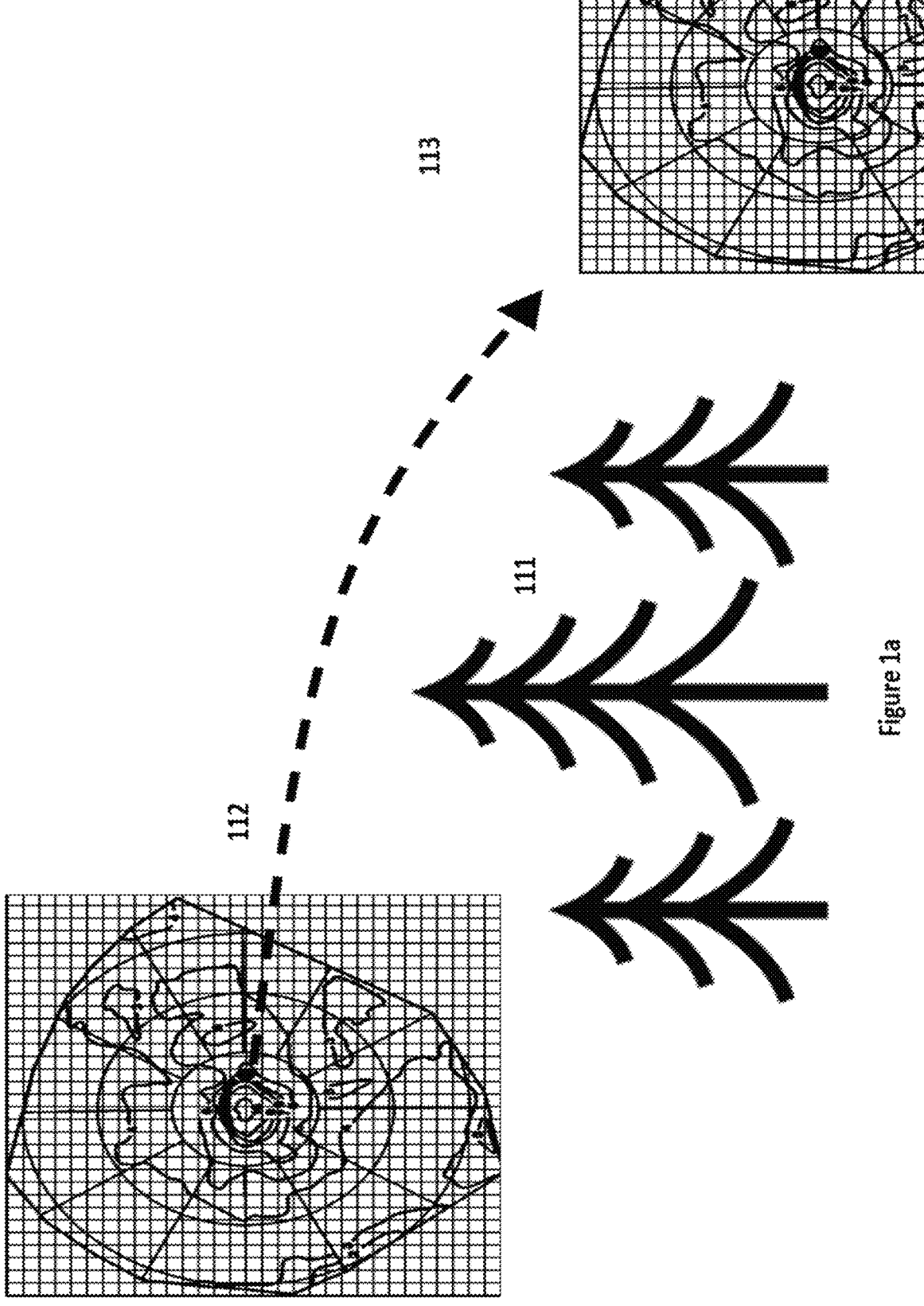
FIG. 1A shows an abstracted view of advanced foveation techniques as applied to an image in accordance with various embodiments of the invention.

FIG. 1a shows analogously the same foveation method shown in FIG. 1, but indicates the intended application and representation of the HRM to foveation, providing the additional benefits of the invention. One example of how HRM foveation applying the invention is used to advantage is to treat S, M, L sensors as having individualized spatial density and hence different spatial optimization. Thus a green perimeter foveated region may have a different spatial density than an overlapping blue region, as appropriate to the sensors. In prior art all color sensors were aggregated and this separation and differentiation of spatial attributes was not possible. Another example would be to have a different temporal density correspond to different density of rod sensors in a specific region, such as a halo ring twenty degrees from the fovea. Using prior art this type of temporal blending would not be possible.

Figure 1B:
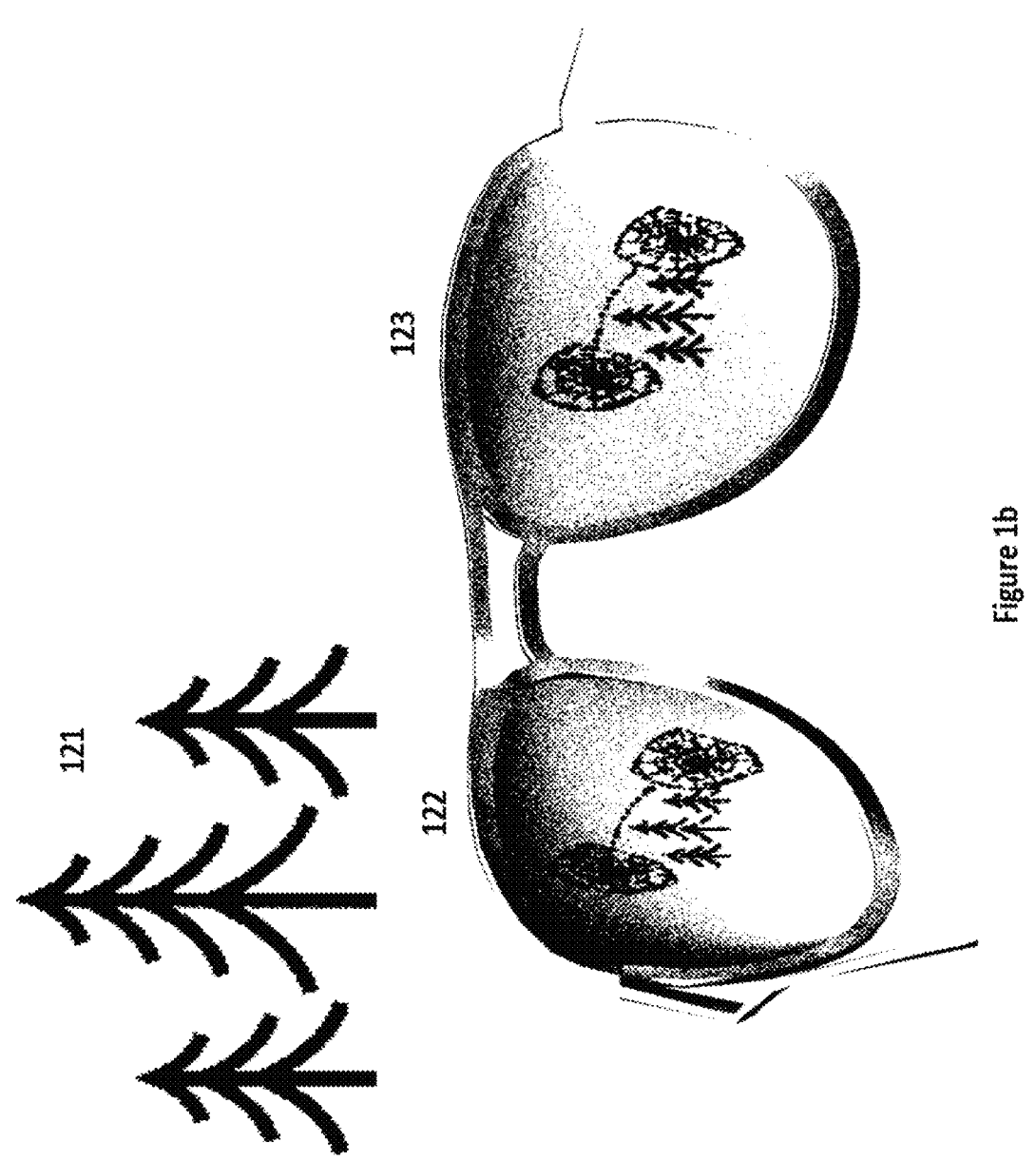
FIG. 1B shows an abstracted view of advanced foveation techniques as applied to an image in a stereo viewing environment in accordance with various embodiments of the invention.

FIG. 1b shows conceptually the same basic foveation method as in FIG. 1 but indicates the intended application of the HRM to dual-display stereo foveation. An example benefit of the invention is the distribution of the same foveation parameters to two or more distinct remote rendering systems, whereas current art would only share that information on a single GPU.

Figure 2:
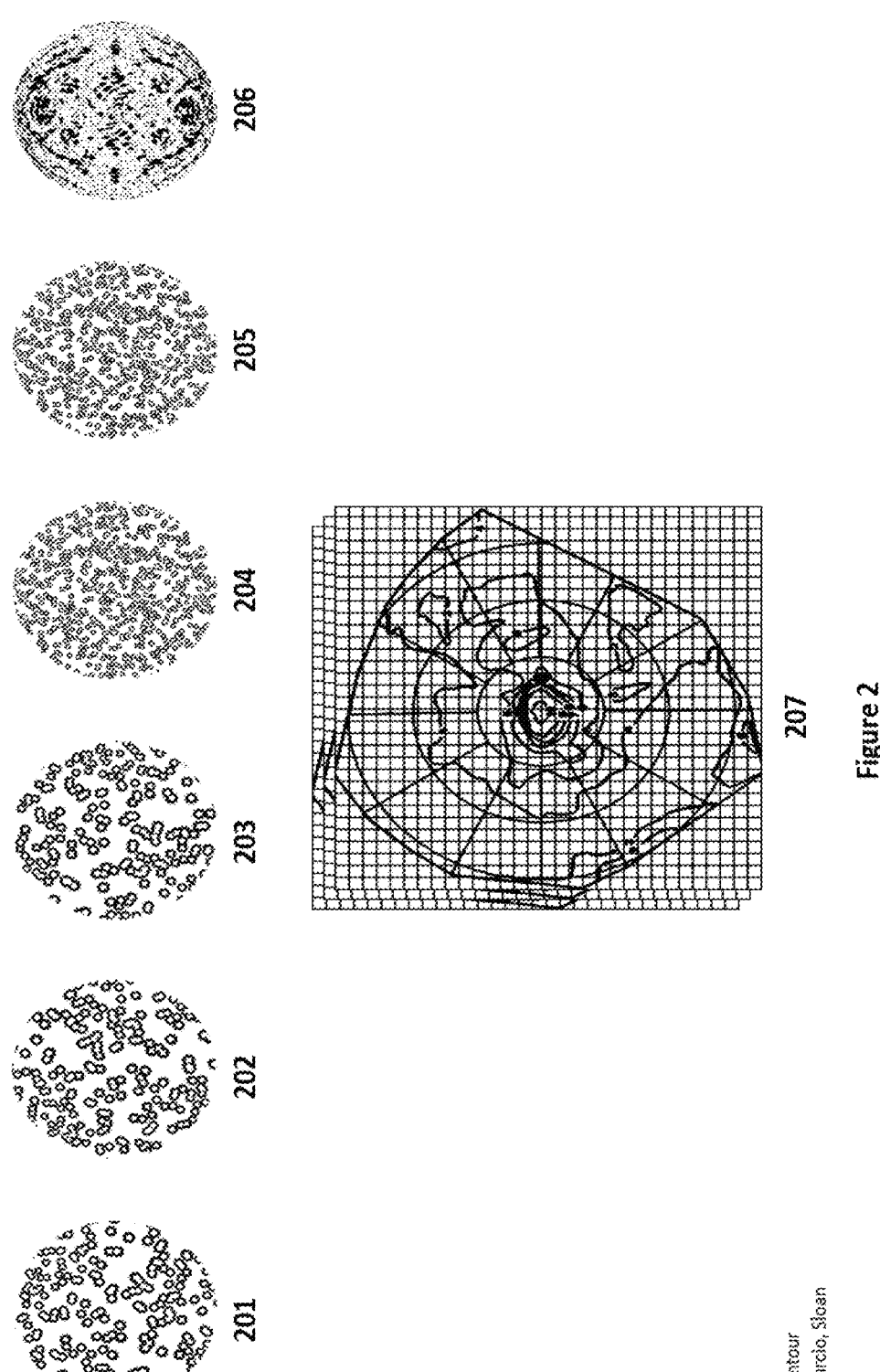
FIG. 2 shows an abstracted view of data from the Human Visual System as processed and placed in a Hyperpixel Retinal Map in accordance with various embodiments of the invention.

FIG. 2 shows an abstracted view of the composition of a simple HRM applying the invention. The intention is for data to be ingested into an HRM and structured with suitable data substructures which may include spatial data, temporal data, functions and so on.

In FIG. 2, example (artificial) source data from the retina is shown with in this case an approximate polar mapping of representative data. 201 consists of a hypothetical dataset providing complete retinal cone information for the Red (or "L") photosensor of the spheroid interior of the retina, including derived density of those cones at a high resolution and datapoints indicating salient datapoint information, for example wavelength sensitivity, trigger thresholds and dynamic range. Similarly, 202 indicates supports of Green or "M" wavelength range cone data. Similarly, 203 indicates support for Blue or "S" wavelength range cone data. Similarly, 204 indicates support for Rod photosensor data, which may be substantially different from the cone data. Similarly, 205 indicates HRM ingestion of photosensitive ganglia sensor data, which may have a more complex data structure representing not just the presence of sensors but occlusion, translucency and photonic reflection characteristics at depth, as an example. 206 indicates HRM data structures associating sensors with their connectivity, which may be between kinds of sensors. 207 indicates the aggregate HRM representation of data, with any necessary conversion of high resolution or potentially sparse or irregular data from the retina, processing to interpolate, extrapolate, smooth or structure that data optimally for inclusion in the HRM and subsequent essential system coordination, including appropriate variants and conditional versions. This preparation and processing may include quantization or isocontouring of that data, or creation of sub-data structures that map to non-regular or alternate structures such as polar coordinate systems, or other regular or non-regular data structures as would be considered by those skilled in the art of data sampling, structuring and access. It may also include masking or other attributes, such as nasal view occlusion of the user, perimeter limitations or attributes of the display device, and the optic nerve blind spot.

Expanding on FIG. 2, another preferred embodiment of the invention demonstrates in more detail its flexibility and the intent of the invention. It also highlights the inability of prior art to implement such as feature. This example is not intended to be limiting and demonstrates more clearly how access via the HRM to multiple sensor data and their interaction is beneficial, and how that serves to coordinate a feature between devices in a network. Applying the same type of data provided in FIG. 2, the red (L) wavelength cone data for the entire retina is first processed to create a 2-dimensional point-cloud which is projected with a polar projection. A nearest neighbor algorithm is applied, whereupon datapoints are gathered according to some threshold parameter. Each final point cloud point then represents one or more red cone sensors at each threshold datapoint, and they are now interpreted as a red sensitivity function. When applied to rendering, for instance, HRM sensitivity regions will be mapped to pixels, and pixels with zero red sensors will not generate red color when the foveal HRM is mapped to screen space according to eye tracking. Pixels mapped to the maximum possible value are assumed to allow full rendering of red from a pixel shader performing the rendering. Pixels with red values falling in between are linearly mapped with a portion of the shaded red value (although another function could be applied).

A subtle new temporal function is also enabled. If a low representative red cone value such as threshold 1 is indicated, this pixel will only be shaded with a proportional red value every third frame, for example. It will be clear to those skilled in the art this is approximating the impact of red wavelength photon sensors over time. This provides multiple benefits. The pixel is compressed 3:1, as the shader device on the network and the display device on the network are both fully aware of the processed HRM and agree not to send the intervening two versions of the red data for the pixel. It also allows re-use of this threshold data to create a separate red contrast isocontour map which is at higher granularity than prior art foveal contrast maps. This may then be used alone for red color channel contrast enhancement processing in the displayed image, or combined with similar contrast isocontours for other cones and the rod isocontours.

It would be readily apparent to those skilled in the art this approach could be extrapolated and expanded to include various data subsets, supersets and additional processing for each sensor data as well as combinations and permutations of that data for advanced foveal processing.

Figure 3:
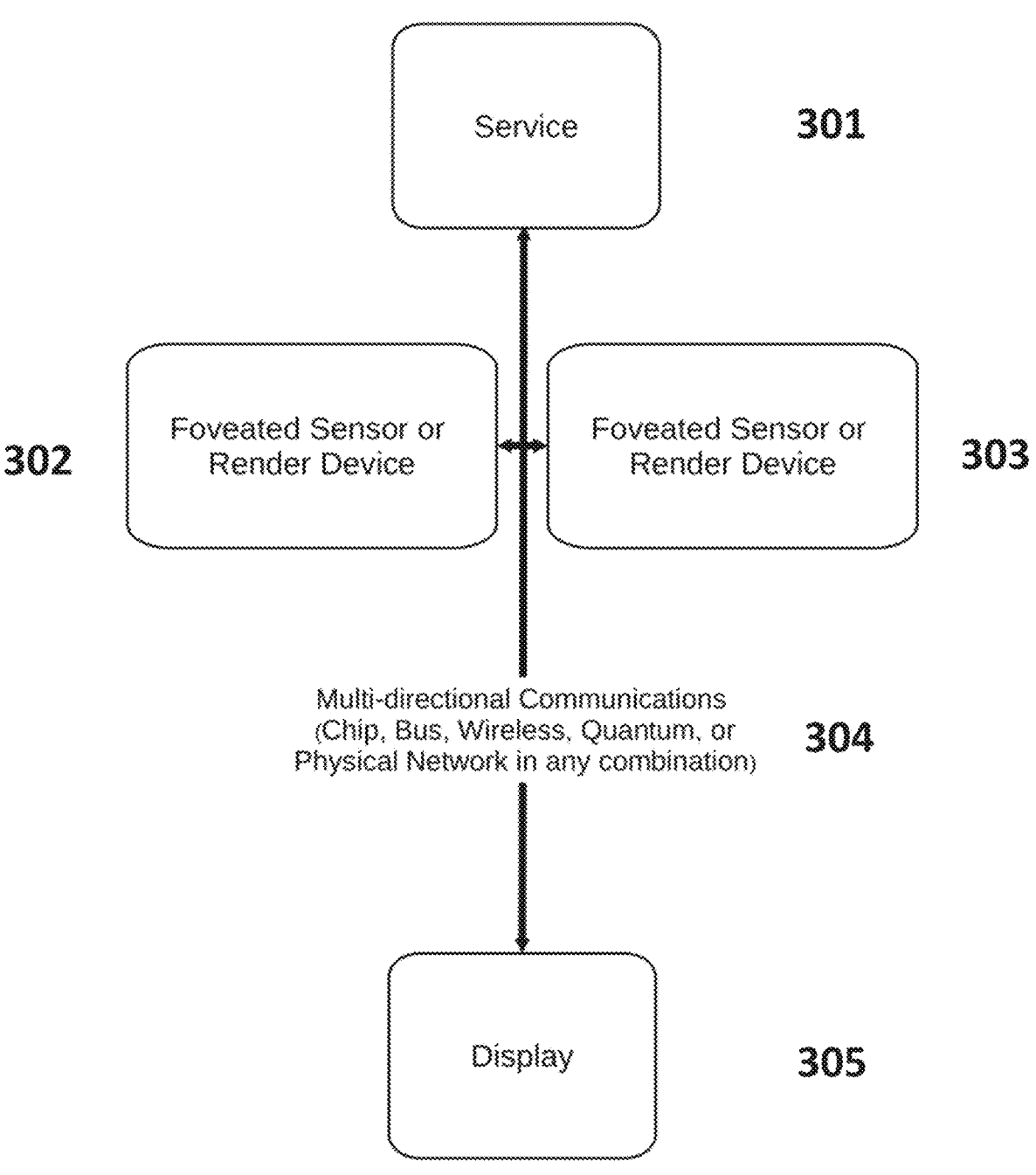
FIG. 3 shows an abstracted view of a service with multiple foveated nodes, in accordance with various embodiments of the invention.

FIG. 3 shows an exemplary flowchart of a service with multiple foveated nodes including the service node or nodes, one or more sensor or render nodes, and one or more display nodes. The service 301 would coordinate distribution of the HRM, capabilities of each node of the system and ongoing updates of optimization parameters such as cost or performance. Nodes 302 and 303 represent typical foveation nodes, such as a render device or an image capture device. Applying the invention, they are not necessarily symmetrical in any fashion. 304 indicates any network or combination of networks connecting the nodes. 305 indicates a display node, typically associated with an end user human but specifically not limited to that since a consumer of foveated imagery could be otherwise, for instance a machine learning algorithm.

Figure 3A:
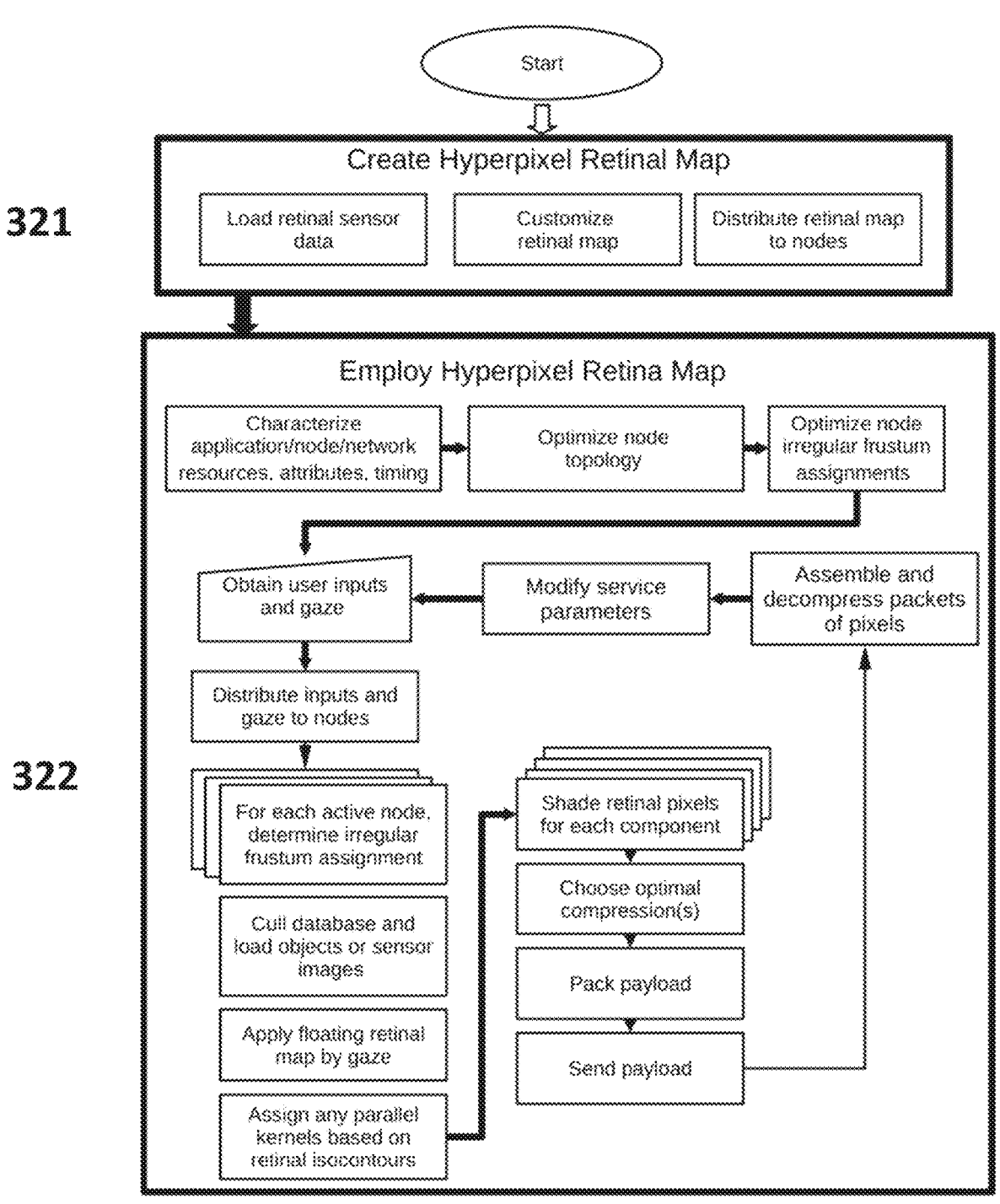
FIG. 3a shows a flowchart of a service employing the Hyperpixel Retinal Map, in accordance with various embodiments of the invention.

FIG. 3a shows a flowchart of a typical service, with more detail of example processes. 321 indicates the inception and distribution of the HRM within a service, and 322 details typical use of the HRM in a real-time distributed foveated rendering system, beginning with characterizing the application/node/network in terms of resources, attributes and timing, followed by optimizing node topology and optimizing node irregular frustum assignments. User inputs and gaze are obtained and distributed to nodes. For each active node irregular frustum assignments are determined. Then the database is culled and objects or sensor images are loaded, a floating point retinal map is applied by gaze, and any parallel kernels are assigned based on retinal isocontours. Retinal pixels are shaded for each component, optimal compression strategies are chosen, and the payloads are packed and sent. The packets of pixels in the payload are assembled and decompressed, and used to modify service parameters which are then fed back into the process where user inputs and gaze are obtained.

Note representation in 322 of multiple rendering nodes, compression by each node, compositing of the data distributed by each node. Also note in 322 the example demonstrates advanced features enabled by the invention, such as flexible irregular frustum assignment, where for example each rendering node can be asymmetric in capabilities and visual assignment, such as overlapping frustums, non-rectangular frustums, depth isolated frustums, temporal or stereo specific frustums, per pixel or channel frustums, per object frustums, per isocontour frustums, or any other arbitrary coordinated assignment by the service. In common use, the pixels generated by these disparate distributed nodes would be assembled and composited on an ultimate display.

Another preferred embodiment demonstrates integration of the Hyperpixel Retinal Map with "pass-through" video integrated within stereo immersive virtual reality glasses. These types of system have one or more external facing cameras which can assist in 6DOF (six degrees of freedom) orientation as well as capture visual or other spectral data for processing such as scene and hand recognition, and additionally serve as a window to the outside world through otherwise possibly opaque virtual reality glasses. Applying the HRM, each eye track would allow optimization of the sampling of the camera data according to the selected interpretation of the HRM and the needs of the recognition. For instance, a user may focus on a pen on a table. The foveated HRM would direct the camera capture system for each eye to apply more power and detail to the area of interest. The foveated HRM would also direct the integrated LIDAR camera to focus its array and optimized data sampling to the fovea and other areas as described in the HRM. Thus the external view of the pen could be optimized or enhanced, and the augmented rendering of the matching virtual object could be optimized as well. The augmented rendering of the user's fingers and hand could also be optimized. Subsequent rendering and merging of the external imagery and the synthetic imagery would follow use of HRM coordination, including available depth information obtained from either the LIDAR and/or stereo visual information derived from the 6DOF subsystem.

Another preferred embodiment demonstrates integration of the Hyperpixel Retinal Map and extends the above to a very full-features system. In addition to already integrating the HRM for each eye as above in the pass-through video example, the system would coordinate distribution of the HRM with 12 (or more, as example) external systems on the network. In this embodiment. Two external nodes participating from an Edge server facility would render the synthetic foveas of each viewpoint at 120 Hz as described by the HRM. The rendered pixels would be messaged back to the user virtual reality headset for composition with the pass-through video. Two additional render nodes would be responsible for rendering at 240 Hz a "halo" isocontour described in the HRM, corresponding to a mid-peripheral area for each user eye which contains the highest threshold of rod photoreceptors. These two renderings would serve to increase the temporal clarity of those areas of the display and would also be fused via compositing with the final display to the user. Four additional external rendering nodes per eye would render other portions of the display area as described in the HRM. One additional external node would receive HRM-described compressed depth data from the LIDAR capture, and render both stereo views of the pencil and hands, allowing greater accuracy in determining the real-pencil's position, and modeling and rendering of the artificial pencil's depth.

Another preferred embodiment integrating use of the HRM would extend the above example of a coordinated distributed multi-node system to include asymmetric combinations of resources. In addition to the multiple sources described above, one cloud service could render using powerful GPU clusters the high complexity background in the scene and include depth (Z) information in the HRM messaging, a less powerful specialized monochromatic text-antialiasing server from a different service provider could render a high resolution overlay with detailed alpha transparency as described in the HRM, and an on-demand authorized private renderer from a low-latency neighbor service could be selected to provide the masked, foreground peripheral isocontour pixels. All of the pixels could either be assembled on the headset or directed to a nearby compositor prior to compressed transmission to the headset, directed by the structure of the HRM.

Another preferred embodiment demonstrating usage of a customized Hyperpixel Retinal Map in a remote operation system intended to optimally and safely fight a fire. The user HRM would be coordinated with a remote infrared CCD-equipped drone. The eye-tracked foveated infrared capture would allow the user to apply their experience to scan the scene for optimal attention at higher resolution than possible for entire scene capture. A stereo view or LIDAR enhancement would allow more accurate registration of the remote scene, and extend the system as would the augmented system above to include optimized rendering and overlay of a synthetic terrain or object database to create more complete situational awareness for the operator. That operator or others could share this information and direct in similar fashion remote drones which had additional functions, such as extended multiple-tether and hybrid autonomous and human guided high pressure firefighting targeting. In total, the system could be deployed by a rugged portable firefighting truck with local communications as well as backhaul network services.

Another preferred embodiment demonstrating usage of a customized Hyperpixel Retinal Map is the explicit recognition of and use of the user blind spot for each eye. This area allows for example masking of the unviewable optic nerve area and hence reduction of creation, transmission or compositing associated with that area.

Another preferred embodiment demonstrating usage of a customized Hyperpixel Retinal Map which indicates optimized quantization of any data, such as reduced or increased bit representation for cone-associated data due to color blindness or display device characteristics. It is the intention this could be customized at a high level, for example per pixel in the display, or per rexel in the source processing of the HRM.

Another preferred embodiment demonstrating usage of a customized Hyperpixel Retinal Map is the ability to associate different sensor data in any combination with variable functions. For example, the behavior of the image system may vary depending on interactions of the red cone specifically with the green cone, and that interaction may vary depending on spatial, temporal or bandwidth ranges.

Another preferred embodiment demonstrating usage of a customized Hyperpixel Retinal Map is the customization of automated analysis based on HRP data. For example, dynamic object recognition functions may be best applied in peripheral zones instead of focal zones or reduce computational workload by limiting the threshold of data (such as color bit-depth) in those areas.

Another preferred embodiment demonstrating usage of a customized Hyperpixel Retinal Map is its application in compositing. For example, multiple overlapping pixels produced and composited in a distributed image system may require different degrees of alpha blending accuracy dependent on the map. As a clarifying example, alpha bit depth for foveal data may be assigned at 6 bits per ultimate pixel, whereas another zone may require 2 bits per pixel for composite blending.

Another preferred embodiment demonstrating usage of a customized Hyperpixel Retinal Map is application to non-obvious and non-visual data. For example, a braille-like audible interpretation of sensor data could be employed, or depth-sensing LIDAR could be incorporated.

Another preferred embodiment applies the HRM data for photosensitive ganglia to assist the application regulating energy and brightness of a scene, registering and optionally deliberately triggering the pupillary response system of the user to assist in management or optimize effect or usage.

Another preferred embodiment applies the HRM data in parallel to multiple image recognition and machine learning systems either simultaneously or asynchronously with the primary destination of the image. The purpose of this embodiment is to allow iterative enhancement of an image or dynamic improvement to the HRM itself for the benefit of the overall system. This can also be interpreted to allow multiple viewers to share the same image or to view or modify portions of that image.

Another preferred embodiment applies the HRM data obtained for the retinal network structure to optimize use of interactions of retinal sensors. For example, the structure of the neural network connecting cones may be interpreted to create another dataset for contrast, with potentially widely different resolution or attributes for different parts of the retina. Different network, network density, bandwidth and sensor interaction data could be used for multiple purposes, as would readily be seen by those skilled in the art.

While the invention has been described in terms of preferred embodiments, those skilled in the art will recognize that the invention can be practiced with modification within the spirit and scope of the appended claims.

What is claimed is:

1. An image foveation system, comprising:
a hyperpixel system further including a hyperpixel data repository and a hyperpixel retinal map, the hyperpixel retinal map corresponding to a human visual system and mapping to the hyperpixel data repository;
a user display system that tracks a user gaze upon an image source enabling the hyperpixel system to distinguish between image source components impinging upon a fovea of a user retina and image source components impinging upon a periphery of the user retina;
wherein the hyperpixel system generates for the user display updates to the image source when needed for changes in the user gaze, the updates being responsive to the human visual system of the user as reflected in the hyperpixel retinal map, including at least updates responsive to user sensitivities at the fovea of the user retina and updates responsive to user sensitivities at the periphery of the user retina.

2. An image foveation system as in claim 1, wherein user sensitivities at the fovea of the user retina are translated by the hyperpixel system into more color and higher resolution and update frequencies as compared to user sensitivities at the periphery of the user retina where a higher density of rods reflects heightened sensitivity to motion.

3. An image foveation system as in claim 1, wherein different user sensitivities at the fovea of the user retina as compared to the periphery of the user retina are translated by the hyperpixel system into updates which are asynchronous across image source components.

4. An image foveation system as in claim 1, wherein the hyperpixel retinal map enables definition of image source components using isocontours, with updates more frequently for components nearer the fovea and updates less frequently for components further from the fovea.

5. An image foveation system as is claim 4, wherein processing of different image source components is distributed to different processors.

6. An image foveation system as is claim 5, wherein at least some of the different processors are located in a network cloud.

7. An image foveation system as is claim 1, wherein the hyperpixel data repository is distributed among a plurality of storage locations.

8. An image foveation system as is claim 2, wherein a different temporal density of updating corresponds to different density of rod sensors in different image components being updated.

9. An image foveation system as is claim 1, further comprising a stereo display wherein foveation parameters for each of the stereo displays are distributed to two or more distinct remote rendering systems for processing.

10. An image foveation system as is claim 9, wherein the stereo display includes nasal view occlusion of the user.

11. An image foveation method, comprising:
establishing a hyperpixel system further including a hyperpixel data repository and a hyperpixel retinal map, the hyperpixel retinal map corresponding to a human visual system and mapping to the hyperpixel data repository;
using a display system that tracks a user gaze upon an image source enabling the hyperpixel system to distinguish between image source components impinging upon a fovea of a user retina and image source components impinging upon a periphery of the user retina;
wherein the hyperpixel system generates for the user display updates to the image source when needed for changes in the user gaze, the updates being responsive to the human visual system of the user as reflected in the hyperpixel retinal map, including at least updates responsive to user sensitivities at the fovea of the user retina and updates responsive to user sensitivities at the periphery of the user retina.

12. An image foveation method as in claim 11, wherein user sensitivities at the fovea of the user retina are translated by the hyperpixel system into more color and higher resolution and update frequencies as compared to user sensitivities at the periphery of the user retina where a higher density of rods reflects heightened sensitivity to motion.

13. An image foveation method as in claim 11, wherein different user sensitivities at the fovea of the user retina as compared to the periphery of the user retina are translated by the hyperpixel system into updates which are asynchronous across image source components.

14. An image foveation method as in claim 11, wherein the hyperpixel retinal map enables definition of image source components using isocontours, with updates more frequently for components nearer the fovea and updates less frequently for components further from the fovea.

15. An image foveation method as is claim 14, wherein processing of different image source components is distributed to different processors.

16. An image foveation method as is claim 15, wherein at least some of the different processors are located in a network cloud.

17. An image foveation method as is claim 11, wherein the hyperpixel data repository is distributed among a plurality of storage locations.

18. An image foveation method as is claim 12, wherein a different temporal density of updating corresponds to different density of rod sensors in different image components being updated.

19. An image foveation method as is claim 11, further comprising a stereo display wherein foveation parameters for each of the stereo displays are distributed to two or more distinct remote rendering systems for processing.

20. An image foveation system as is claim 19, wherein the stereo display includes nasal view occlusion of the user.

\* \* \* \* \*